(12) United States Patent
Trieu et al.

(10) Patent No.: US 8,795,368 B2
(45) Date of Patent: Aug. 5, 2014

(54) EXPANDABLE IMPLANT SYSTEM AND METHODS OF USE

(75) Inventors: Hai H Trieu, Cordova, TN (US); Sachin P. Budhabhatti, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 477 days.

(21) Appl. No.: 13/095,634

(22) Filed: Apr. 27, 2011

(65) Prior Publication Data

US 2012/0277865 A1 Nov. 1, 2012

(51) Int. Cl.
*A61F 2/44* (2006.01)
*A61F 2/30* (2006.01)
*A61F 2/28* (2006.01)
*A61F 2/46* (2006.01)

(52) U.S. Cl.
CPC ....... *A61F 2/442* (2013.01); *A61F 2310/00179* (2013.01); *A61F 2002/30364* (2013.01); *A61F 2002/30433* (2013.01); *A61F 2310/00023* (2013.01); *A61F 2310/0097* (2013.01); *A61F 2310/00017* (2013.01); *A61F 2002/30677* (2013.01); *A61F 2002/30779* (2013.01); *A61F 2002/30543* (2013.01); *A61F 2002/30153* (2013.01); *A61F 2310/00293* (2013.01); *A61F 2002/2835* (2013.01); *A61F 2002/30482* (2013.01); *A61F 2002/30372* (2013.01); *A61F 2002/3008* (2013.01); *A61F 2002/30062* (2013.01); *A61F 2/447* (2013.01); *A61F 2002/30777* (2013.01); *A61F 2/4611* (2013.01); *A61F 2310/00029* (2013.01); *A61F 2002/30504* (2013.01); *A61F 2002/2817* (2013.01); *A61F 2310/00359* (2013.01); *A61F 2002/30879* (2013.01); *A61F 2002/30538* (2013.01)
USPC .................................... 623/17.11; 623/17.16

(58) Field of Classification Search
USPC ............................................. 623/17.11–17.16
See application file for complete search history.

(56) References Cited

U.S. PATENT DOCUMENTS

| | | | |
|---|---|---|---|
| 5,658,336 A | 8/1997 | Pisharodi | |
| 5,800,547 A * | 9/1998 | Schafer et al. | 623/17.16 |
| 6,179,873 B1 * | 1/2001 | Zientek | 623/17.11 |
| 6,190,387 B1 * | 2/2001 | Zucherman et al. | 606/249 |
| 6,371,987 B1 * | 4/2002 | Weiland et al. | 623/17.11 |
| 6,527,803 B1 * | 3/2003 | Crozet et al. | 623/17.11 |
| 6,770,096 B2 * | 8/2004 | Bolger et al. | 623/17.16 |
| 7,824,427 B2 | 11/2010 | Perez-Cruet et al. | |
| 8,267,997 B2 * | 9/2012 | Colleran | 623/17.11 |
| 8,366,774 B1 * | 2/2013 | Bruffey et al. | 623/17.11 |
| 8,540,769 B2 * | 9/2013 | Janowski et al. | 623/17.11 |
| 8,545,562 B1 * | 10/2013 | Materna et al. | 623/17.11 |
| 2002/0165613 A1 * | 11/2002 | Lin et al. | 623/17.11 |
| 2003/0187436 A1 * | 10/2003 | Bolger et al. | 606/61 |
| 2005/0038512 A1 * | 2/2005 | Michelson | 623/17.11 |
| 2006/0095136 A1 * | 5/2006 | McLuen | 623/23.47 |
| 2006/0142859 A1 * | 6/2006 | McLuen | 623/17.11 |
| 2006/0224241 A1 * | 10/2006 | Butler et al. | 623/17.15 |
| 2006/0241621 A1 * | 10/2006 | Moskowitz et al. | 606/72 |
| 2008/0091269 A1 * | 4/2008 | Zipnick et al. | 623/17.13 |

(Continued)

*Primary Examiner* — David Bates

(57) ABSTRACT

An implant includes a first component including a wall that defines a first surface and a second surface. The first surface defines a first opening and the second surface defines a second opening. The second opening is spaced apart from the first opening to define a cavity therebetween. A second component is supported by the first component and configured for movement relative thereto. The second component is movable between a first configuration such that the second component is disposed between the first opening and the second opening within the cavity and a second, expanded configuration such that the second component simultaneously passes through the first and second openings to extend from the cavity. Methods of use are also disclosed.

16 Claims, 9 Drawing Sheets

(56) References Cited

U.S. PATENT DOCUMENTS

| | | | |
|---|---|---|---|
| 2009/0099601 A1* | 4/2009 | Aferzon et al. | 606/246 |
| 2009/0312837 A1 | 12/2009 | Eisermann et al. | |
| 2010/0049324 A1 | 2/2010 | Valdevit et al. | |
| 2010/0137989 A1* | 6/2010 | Armstrong et al. | 623/17.16 |
| 2011/0208311 A1* | 8/2011 | Janowski | 623/17.16 |
| 2011/0230971 A1* | 9/2011 | Donner et al. | 623/17.16 |

* cited by examiner

EXPANDABLE IMPLANT SYSTEM AND METHODS OF USE

TECHNICAL FIELD

The present disclosure generally relates to medical devices, systems and methods for the treatment of musculoskeletal disorders, and more particularly to an interbody implant system and method that provides stabilization and height restoration for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY OF THE INVENTION

Accordingly, an interbody implant system and method is provided that provides stabilization and height restoration for treating a vertebral column. It is contemplated that the interbody implant system includes a spinal implant, which is movable between a first configuration and a second configuration. It is further contemplated that the implant system and method may be employed for an arthrodesis treatment using minimally invasive and percutaneous techniques.

In one embodiment, a spinal implant is provided. The spinal implant a first component including a wall that defines a first surface and a second surface. The first surface defines a first opening and the second surface defines a second opening. The second opening is spaced apart from the first opening to define a cavity therebetween. A second component is supported by the first component and configured for movement relative thereto. The second component is movable between a first configuration such that the second component is disposed between the first opening and the second opening within the cavity and a second, expanded configuration such that the second component simultaneously passes through the first and second openings to extend from the cavity.

In one embodiment, an interbody implant system is provided. The interbody implant system includes a support including a first end wall, a second end wall and at least one side wall extending therebetween. The walls define a first surface that defines a first opening that is substantially disposed in a first plane and a second surface that defines a second opening that is substantially disposed in a second plane. The second plane is spaced apart from the first plane to define a cavity therebetween. The first end wall and the second end wall each include an elongated slot. A body defines a longitudinal axis and extends between a first end and a second end. The first end is supported with the slot of the first end wall and the second end is supported with the slot of the second end wall. The body includes a first vertebral engaging surface and a second, opposing vertebral engaging surface disposed along the longitudinal axis. The body is disposable between a collapsed configuration such that the first and second vertebral engaging surfaces are disposed in the cavity and an expanded configuration such that the body is rotated about the longitudinal axis such that the first and second vertebral engaging surfaces pass through the first and second openings of the support and the body linearly translates relative to the support. An instrument includes an engagement member configured to engage at least one of the first end and the second end of the body and rotate the body about the longitudinal axis. At least one agent is configured for disposal with at least one aperture of the support and the body.

In one embodiment, an interbody implant system is provided. The interbody implant system includes a support frame defining a central longitudinal axis and including a first end wall and a second end wall disposed in substantially parallel relation. The first and second end walls are connected by spaced apart side walls. The walls of the support frame define an upper surface and a lower surface. The upper surface defines an upper opening and the lower surface defines a lower opening. The upper opening is spaced apart from the lower opening to define a cavity therebetween. The first end wall and the second end wall each define a slot. Each slot defines a first keyway, a second keyway and a locking element. A cam body defines a longitudinal axis and extends between a first end supported in the slot of the first end wall and a second end supported in the slot of the second end wall. The cam body includes a first surface configured to engage a first vertebral surface and a second surface configured to engage a second vertebral surface. The cam body including a first flange configured to engage the upper surface of the support frame and a second flange configured to engage the lower surface. The cam body is disposable between a collapsed configuration such that the first and second vertebral surfaces are substantially disposed in the cavity and the longitudinal axis of the cam body is disposed in a coaxial orientation with the central longitudinal axis of the support frame, and movable to an expanded configuration such that the first and second ends of the cam body are rotatable in the first keyways such that the body is rotated about the longitudinal axis such that the first and second vertebral engaging surfaces pass through the first and second openings of the support frame and the first and second ends are linearly translatable to the second keyways and retained therein by the locking elements, and the flanges engage the upper and lower surfaces respectively to fix the support frame and the cam body in the expanded configuration. A cam driver engages with at least one of the first end and the second end of the cam body to rotate the cam body. At least one agent is configured for disposal with at least one aperture of the support frame and at least one aperture of the cam body.

BRIEF DESCRIPTION OF THE DRAWINGS

The present disclosure will become more readily apparent from the specific description accompanied by the following drawings, in which.

DETAILED DESCRIPTION OF THE INVENTION

Figure 1:
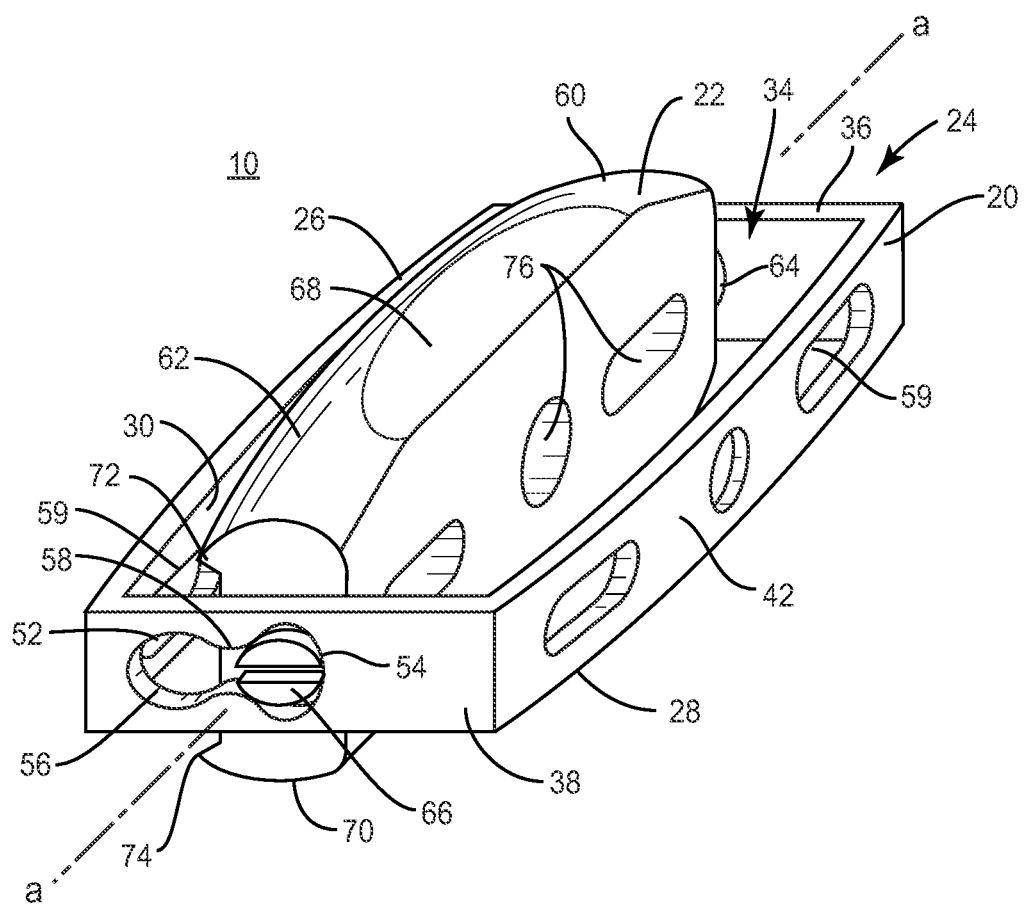
FIG. 1 is a perspective view of one particular embodiment of an implant of a system in accordance with the principles of the present disclosure.
Figure 2:
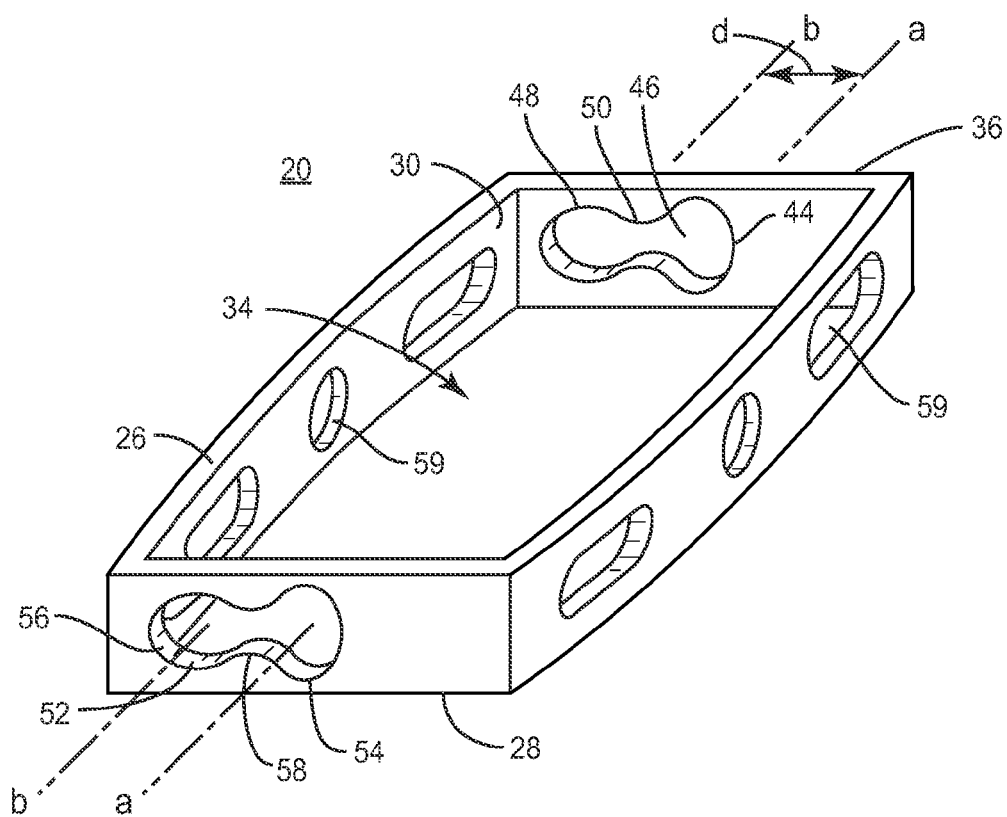
FIG. 2 is a perspective view of a first component of the implant shown in FIG. 1.
Figure 3:
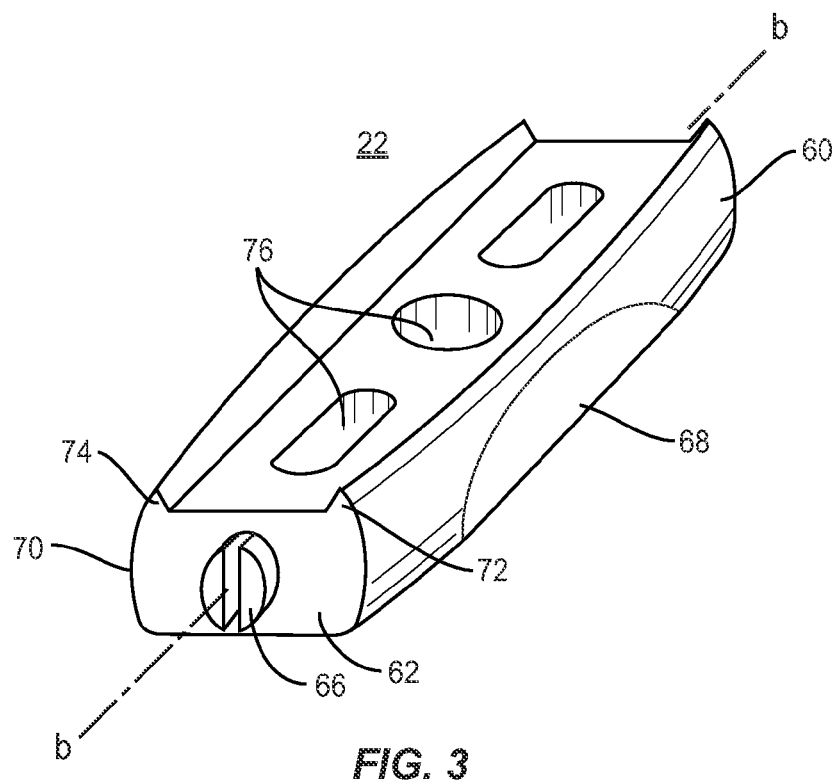
FIG. 3 is a perspective view of a second component of the implant shown in FIG. 1.
Figure 4:
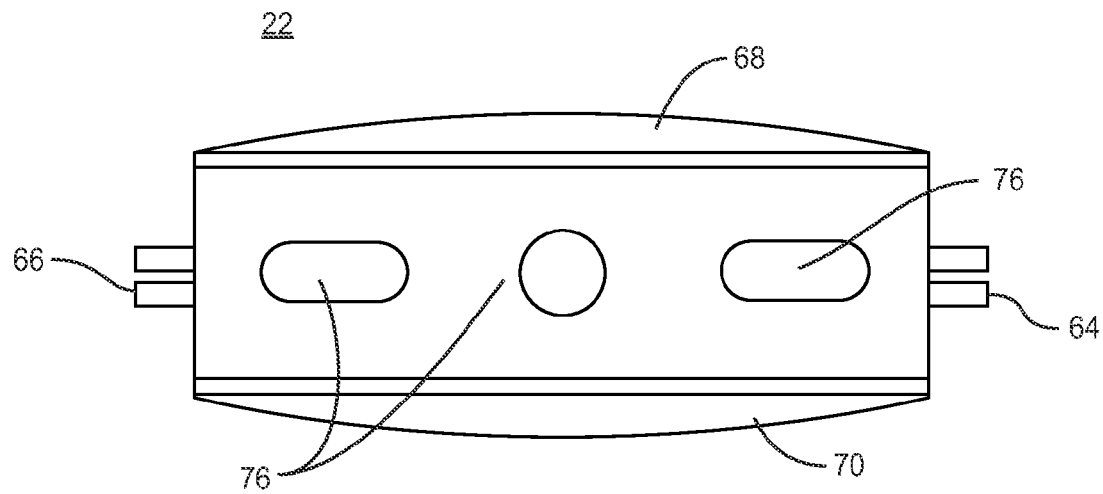
FIG. 4 is a top view of the second component shown in FIG. 3.
Figure 5:
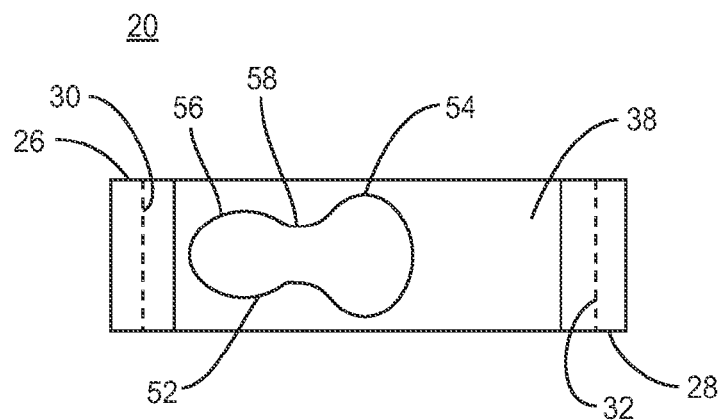
FIG. 5 is an enlarged end view of the first component shown in FIG. 2.
Figure 6:
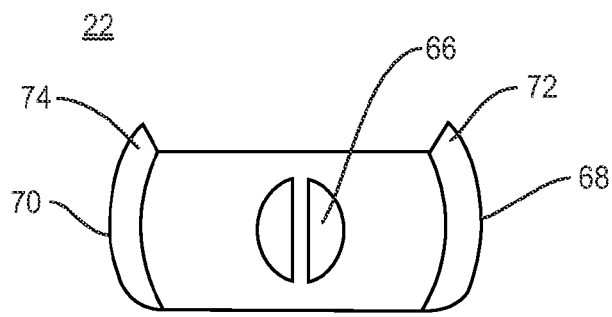
FIG. 6 is an enlarged end view of the second component shown in FIG. 3.

The exemplary embodiments of the interbody implant system and related methods of use disclosed are discussed in terms of medical devices for the treatment of musculoskeletal disorders and more particularly, in terms of an interbody implant that provides stabilization and height restoration for treating a vertebral column. It is envisioned that the interbody implant system may be employed for fusion and fixation treatments to provide decompression, restoration of lordosis and resistance of subsidence into tissue, for example, vertebral endplates. It is further envisioned that the interbody implant system and methods of use disclosed can be employed to obtain fusion of vertebrae through a minimally invasive or percutaneous technique. In one embodiment, the disclosed interbody implant system and methods of use can provide improved spinal treatment with a device that rotates and translates a cam body in a support to create lordosis in vertebrae. It is contemplated that the interbody implant system and methods of use disclosed provide anti-migration and locking of an implant after expansion. It is further contemplated that the interbody implant system and methods of use disclosed provide large volume for post-packing of at least one agent, for example, bone graft.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed interbody implant system may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The present disclosure may also be alternatively employed with procedures for treating the lumbar, cervical, thoracic and pelvic regions of a spinal column. The interbody implant system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of an interbody implant system and related methods of employing the interbody implant system in accordance with the principles of the present disclosure. Alternate embodiments are also disclosed. Reference will now be made in detail to the exemplary embodiments of the present disclosure, which are illustrated in the accompanying figures. Turning now to FIGS. 1-20, there is illustrated components of an interbody implant system in accordance with the principles of the present disclosure.

The components of the interbody implant system can be fabricated from biologically acceptable materials suitable for medical applications, including metals, synthetic polymers, ceramics and bone material and/or their composites, depending on the particular application and/or preference of a medical practitioner. For example, the components of the interbody implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the interbody implant system may have material composites, including the above materials, to achieve various desired characteristics such as strength, rigidity, elasticity, compliance, biomechanical performance, durability and radiolucency or imaging preference. The components of the interbody implant system, individually or collectively, may also be fabricated from a heterogeneous material such as a combination of two or more of the above-described materials.

The interbody implant system includes a spinal implant 10 employed as a stabilization device in fusion and fixation procedures, for example, for patients suffering from a spinal disorder to provide height restoration between vertebral bodies, decompression and/or restoration of lordosis. Spinal implant 10 includes a first component, such as, for example, a support frame 20, and a second component, such as, for example, a cam body 22. Cam body 22 is supported by frame 20 and configured for movement relative thereto, as will be described. The components of the interbody implant system may be monolithically formed, integrally connected or include fastening elements and/or instruments, for example, as described herein.

Frame 20 includes a wall 24 that defines a first surface, such as, for example, a top surface 26 and a second surface, such as, for example, a bottom surface 28. Surface 26 defines a first opening 30 that is substantially disposed in a first plane defined by surface 26. Surface 28 defines a second opening 32 that is substantially disposed in a second plane defined by surface 28. Opening 32 is spaced apart from opening 30 to define an inner cavity 34 of frame 20 therebetween. It is contemplated that the surfaces 26, 28 may be alternately configured such that openings 30, 32 are non-planar, arcuate, offset, undulating or staggered. Surfaces 26, 28 are substantially smooth or even. It is further contemplated that all or only a portion of surfaces 26, 28 may have alternate surface configurations, such as, for example, planar, rough, arcuate, undulating, mesh, porous, semi-porous, dimpled, polished and/or textured according to the requirements of a particular application.

Openings 30, 32 have a substantially rectangular configuration and extend along a longitudinal axis a of frame 20, which corresponds to a center of rotation of implant 10. It is envisioned that openings 30, 32 may have alternate configurations, such as, for example, oval, oblong, triangular, square, polygonal, irregular, uniform, non-uniform, offset, staggered, undulating, arcuate, variable and/or tapered. Inner cavity 34 defines a substantially rectangular and constant volume configuration. It is envisioned that inner cavity 34 may have alternate configurations such as those alternatives described herein.

Frame 20 extends between and wall 24 includes a first end wall 36 and a second end wall 38 disposed in substantially parallel relation. Walls 36, 38 are connected by spaced apart side walls 40, 42, which have an arcuate configuration and are disposed in substantially parallel relation. Walls 36, 38 extend in a transverse orientation relative to axis a. Walls 40, 42 extend in a parallel orientation relative to axis a. It is contemplated that one or all of walls 36, 38, 40, 42 may be disposed at alternate orientations, relative to axis a, for example, perpendicular, parallel and/or other angular orientations such as acute or obtuse, co-axial and/or may be offset or staggered. It is further contemplated that one or all of walls 36, 38, 40, 42 may have alternate configurations such as those alternatives described herein.

End wall 36 defines an elongated slot 44 configured to support cam body 22, as will be described below. Slot 44 defines a first keyway 46 having a substantially oval configuration and a second keyway 48 having a substantially oval configuration disposed in transverse orientation relative to first keyway 46. Keyway 46 is connected to keyway 48 by a locking element portion of slot 44, such as, for example, gates 50 that provide a reduced dimension of slot 44 to fix cam body 22 in a position and prevent movement of cam body 22 from keyway 48. It is envisioned keyways 46, 48 may have alternate configurations such as those alternatives described herein. It is further envisioned keyways 46, 48 may be disposed at alternate orientations such as those alternatives described herein. It is contemplated that slot 44 may include only one or a plurality of locking elements.

End wall 38 defines an elongated slot 52 configured to support cam body 22, as will be described below. Slot 52 defines a first keyway 54 having a substantially oval configuration and a second keyway 56 having a substantially oval configuration disposed in transverse orientation relative to first keyway 54. Keyway 54 is connected to keyway 56 by a locking element portion of slot 52, such as, for example, gates 58 that provide a reduced dimension of slot 52 to fix cam body 22 in a position and prevent movement of cam body 22 from keyway 56. It is envisioned keyways 54, 56 may have alternate configurations such as those alternatives described herein. It is further envisioned keyways 54, 56 may be disposed at alternate orientations such as those alternatives described herein. It is contemplated that slot 52 may include only one or a plurality of locking elements. Frame 20 defines a plurality of openings, such as, for example, apertures 59 that are configured for disposal of at least one agent, as will be described. It is envisioned that frame 20 may include one or a plurality of apertures 59.

Cam body 22 defines a longitudinal axis b and extends between a first end 60 and a second end 62. End 60 defines a key 64 that is supported with slot 44 for relative movement therein. End 62 defines a key 66 that is supported with slot 52 for relative movement therein. Keys 64, 66 each have a substantially oval configuration corresponding to the keyways of slots 44, 52 and define a channel for receiving an instrument that facilitates manipulation of implant 10. It is envisioned keys 64, 66 may have alternate configurations such as those alternatives described herein. Keys 64, 66 are rotatable and linearly translatable with slots 44, 52, respectively, as will be described. Cam body 22 has a uniform configuration. It is contemplated cam body 22 may have alternate configurations such as those alternatives described herein.

Cam body 22 defines a first vertebra engaging surface 68 and a second vertebra engaging surface 70, which extend along axis b and are configured to enhance fixation and/or gripping with vertebral tissue. Surfaces 68, 70 include arcuate and planar portions. It is contemplated that all or only a portion of surfaces 68, 70 may have alternate surface configurations to enhance disposal with frame 20 and/or fixation with tissue such as those alternatives described herein.

Cam body 22 includes a fixation element, such as, for example, a first flange 72 configured to engage surface 26 and a second flange 74 configured to engage surface 28. Flanges 72, 74 extend along axis b and are spaced apart corresponding to the dimension of walls 36, 38. Flanges 72, 74 engage surfaces 26, 28 respectively, to fix frame 20 in a particular configuration with cam body 22, as will be described. It is contemplated that cam body 22 may be fixed with frame 20 employing alternative fixation elements, such as, clips, screws, resilient members and/or adhesive.

Cam body 22 defines a plurality of openings, such as, for example, apertures 76 that are configured for disposal of at least one agent, as will be described. It is envisioned that cam body 22 may include one or a plurality of apertures 76. It is further envisioned that apertures 59, 76 may have alternative configurations such as those alternatives described herein.

In operation, as shown in FIGS. 7-12, spinal implant 10, described above with regard to FIGS. 1-6, is engaged for disposal between a first configuration such that cam body 22 is disposed between openings 30, 32 within inner cavity 34 and a second configuration such that cam body 22 simultaneously passes through openings 30, 32 to extend from inner cavity 34. Spinal implant 10 is engaged with an instrument, such as, for example, a cam driver 100 (FIG. 20) to facilitate actuation of the component parts of spinal implant 10 and disposal thereof in various configurations according to the requirements of a particular surgical application. Cam driver 100 is a surgical tool for manipulating spinal implant 10. Cam driver 100 has a shaft 111 and a handle 112 that extends to a head 110 configured to engage and mate with the channel of key 64 and/or key 66 to rotate and/or translate cam body 22. Head 110 has a tapered configuration for mating with keys 64, 66 in a releasable friction or pressure fit engagement. It is envisioned that head 110 may have alternate configurations such as those described herein.

Figure 8:
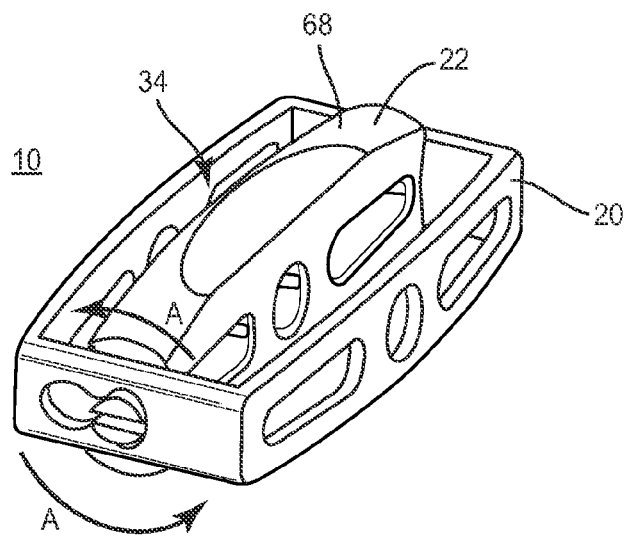
FIG. 8 is a perspective view of the implant shown in FIG. 1.
Figure 9:
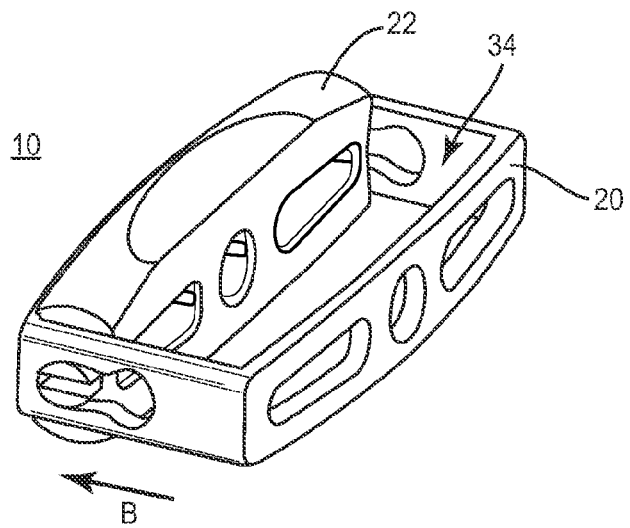
FIG. 9 is a perspective view of the implant shown in FIG. 1.
Figure 11:
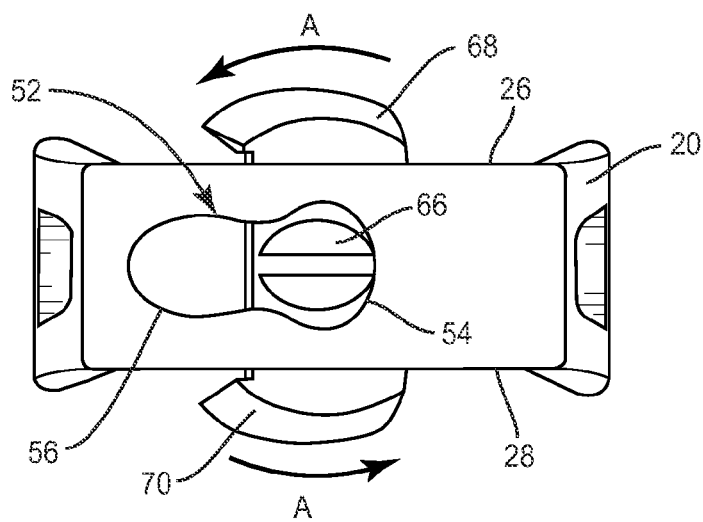
FIG. 11 is an end view of the implant shown in FIG. 1.
Figure 12:
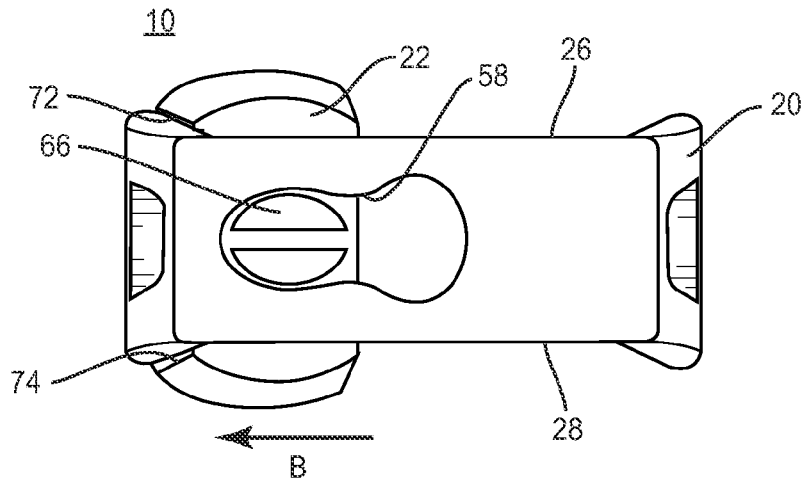
FIG. 12 is an end view of the implant shown in FIG. 1.

Cam driver 100 is manipulated and head 110 is caused to engage the channel of key 64 and/or key 66 to rotate cam body 22 in a selected direction, such as, for example, counter clockwise, as shown by arrows A in FIGS. 8 and 11. Cam driver 100 is further manipulated such that head 110 drives cam body 22 in translation relative to frame 20 in a first axial direction, as shown by arrows B in FIGS. 9 and 12. As such, cam driver 100 is manipulable to rotate and linearly translate cam body 22 relative to frame 20 and axis a, for disposal of spinal implant 10 between the first and second configurations.

Figure 7:
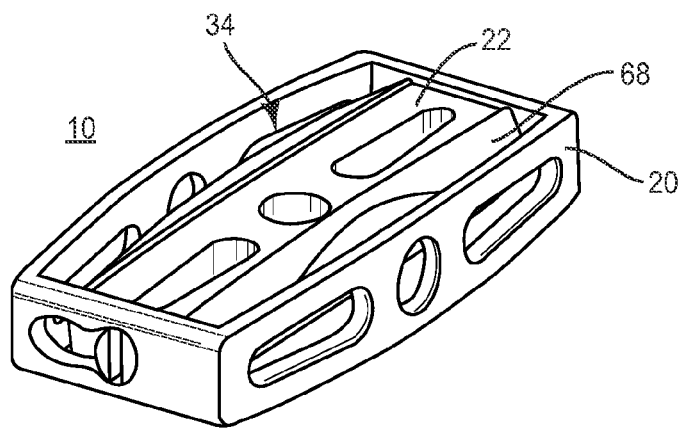
FIG. 7 is a perspective view of the implant shown in FIG. 1.
Figure 10:
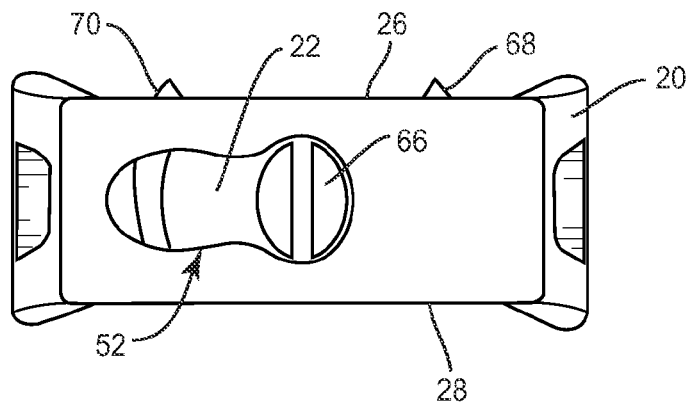
FIG. 10 is an end view of the implant shown in FIG. 1.

In a first configuration, such as, for example, a collapsed configuration, as shown in FIGS. 7 and 10, frame 20 and cam body 22 are disposed in a low profile orientation such that cam body 22 is disposed between openings 30, 32 within inner cavity 34 to facilitate delivery of spinal implant 10 through a minimally invasive or percutaneous surgical pathway. Spinal implant 10 is positioned in a body cavity of a patient for a surgical procedure. Vertebra engaging surfaces 68, 70 are disposed within inner cavity 34.

Upon desired positioning of spinal implant 10 according to the requirements of a particular surgical application, head 110 is mated with key 64 and/or key 66 to rotate cam body 22 in a counterclockwise direction, as discussed above, about the center of rotation of spinal implant 10. Cam body 22 rotates about axis a such that keys 64, 66 rotate relative to keyways 46, 54 within slots 44, 52, and flanges 72, 74 extend over and engage surfaces 26, 28 respectively, to retain frame 20 in a second configuration, such as, for example, an expanded configuration with cam body 22. Vertebra engaging surfaces 68, 70 rotate about axis b of cam body 22 and simultaneously pass through openings 30, 32 to provide an expanded height of spinal implant 10. It is contemplated that flanges 72, 74 may permanently lock or releasably lock spinal implant 10 in the expanded configuration.

In the expanded configuration, head 110 drives cam body 22 in translation relative to frame 20 in a first axial direction, as discussed above. Keys 64, 66 linearly translate in the direction of arrows B through slots 44, 52 to distract and/or snap through gates 50, 58 for disposal in keyways 48, 56. Axis b of cam body 22 is spaced apart a distance d (FIG. 2) from axis a of frame 20 in the expanded configuration. The transverse oval configuration of keyways 48, 56, and gates 50, 58 capture keys 64, 66 and prevent rotation and escape of keys 64, 66 from keyways 48, 56. This configuration facilitates fixation and locking of spinal implant 10 in the expanded configuration. It is contemplated that in the expanded configuration, spinal implant 10 provides vertical expansion to increase vertical spacing in a body cavity for decompression, restoration of lordosis and resistance of subsidence into vertebral endplates. It is further contemplated that spinal implant 10 provides anti-migration and locking of implant 10 after expansion. It is envisioned that gates 50, 58 may permanently lock or releasably lock spinal implant 10 in the expanded configuration.

In one embodiment, spinal implant 10 is disposable in various alternate configurations between the expanded and collapsed configurations. In one embodiment, spinal implant 10 can be collapsed from the expanded configuration to an alternate configuration between the expanded and collapsed configurations, via manipulation of cam body 22 in a second axial direction, opposite to the first axial direction. It is envisioned that reciprocal axial movement of cam body 22 to collapse spinal implant 10 may be desired to reposition or remove spinal implant 10 from a body cavity.

In one embodiment, the interbody implant system includes a plurality of spinal implants 30. It is contemplated that each of the plurality of spinal implants 30 may have various cross section geometry and material configurations relative to other spinal implants 30, and the plurality of spinal implants 30 may have various orientation configurations relative to other spinal implants 30. It is further contemplated that the plurality of spinal implants 10 can be oriented in a side by side engagement, spaced apart and/or staggered.

In assembly, operation and use, the interbody implant system is employed with a surgical procedure such as a fusion treatment of a spine of a patient including vertebrae V, intervertebral disc space I and body areas adjacent thereto, as discussed herein. The interbody implant system may also be employed with other surgical procedures, such as, for example, discectomy, laminotomy, laminectomy, nerve root retraction, foramenotomy, facetectomy, decompression, and spinal, nucleus or disc replacement.

For example, the interbody implant system can be employed with a surgical procedure to provide height restoration between vertebral bodies for treatment of an applicable condition or injury of an affected section of a spinal column and adjacent areas within a body, such as, for example, intervertebral disc space I between the endplate of vertebrae V1 and the endplate of vertebrae V2 of vertebrae V. It is contemplated that spinal implant 10 of the interbody implant system can be inserted with intervertebral disc space I to space apart articular joint surfaces, provide support and maximize stabilization of vertebrae V.

In use, as shown in FIGS. 13-18, to treat the affected section of vertebrae V, a medical practitioner obtains access to a surgical site including vertebrae V in any appropriate manner, such as through incision and retraction of tissues. It is envisioned that spinal implant 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure is performed for treating the spine disorder. Spinal implant 10 is then employed to augment the surgical treatment. It is contemplated that one or all of the components of the interbody implant system can be delivered to the surgical site via manual manipulation and/or a free hand technique. It is further contemplated that the components of the interbody implant system may be inserted posteriorly, and then manipulated anteriorly and/or lateral and/or medial.

Figure 13:
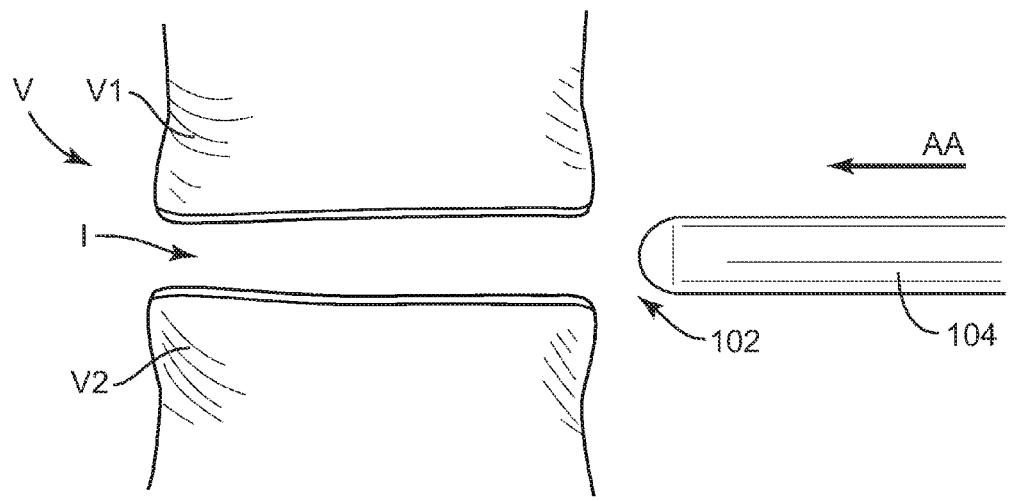
FIG. 13 is a side view of vertebrae and a component of the system in accordance with the principles of the present disclosure.
Figure 14:
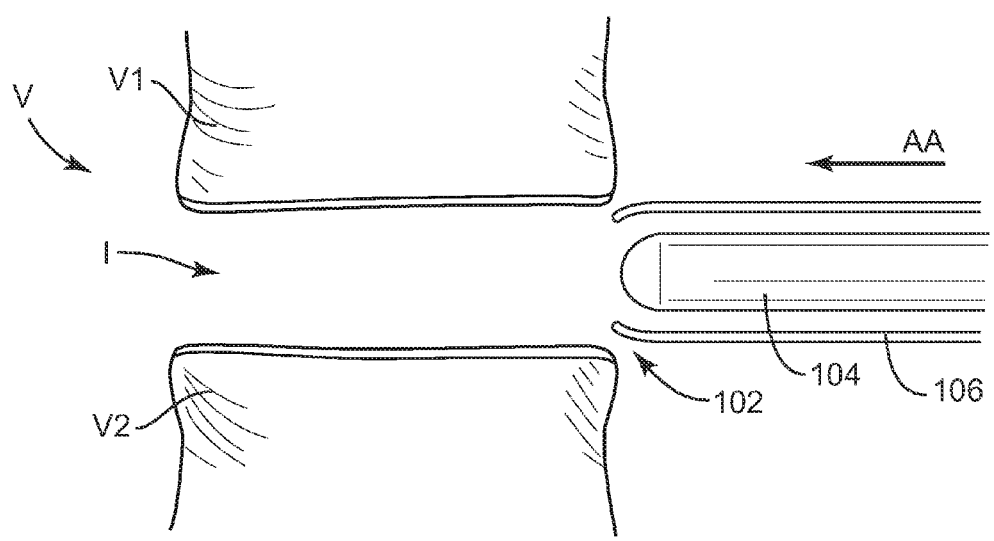
FIG. 14 is a side view of the vertebrae and components of the system shown in FIG. 13.

An incision is made in the body of a patient and a cutting instrument (not shown) creates a surgical pathway 102 for implantation of spinal implant 10 within the patient body, as shown in FIG. 13. A guide instrument 104 is employed to initially distract vertebrae V1 from vertebrae V2, as manipulated in the direction of arrow AA. A sleeve or cannula 106 is used to access intervertebral disc space I, as manipulated in the direction of arrow AA, as shown in FIG. 14, and facilitate delivery and access for components of the interbody implant system. A preparation instrument (not shown) can be inserted within cannula 106 and disposed within intervertebral disc space I. The preparation instrument(s) can be employed to remove some or all of the disc tissue including the disc nucleus and fluids, adjacent tissues and/or bone, corticate, scrape and/or remove tissue from the surfaces of endplates of opposing vertebrae V1, V2, as well as for aspiration and irrigation of the region according to the requirements of a particular surgical application. It is envisioned that the components of the interbody implant system, which may include one or a plurality of spinal implants 10, can be delivered to the surgical site via alternate approaches, such as, for example, delivery through the surgical pathway along a direct lateral approach, a transforaminal lumbar interbody fusion approach and a posterior lumbar interbody fusion.

Figure 15:
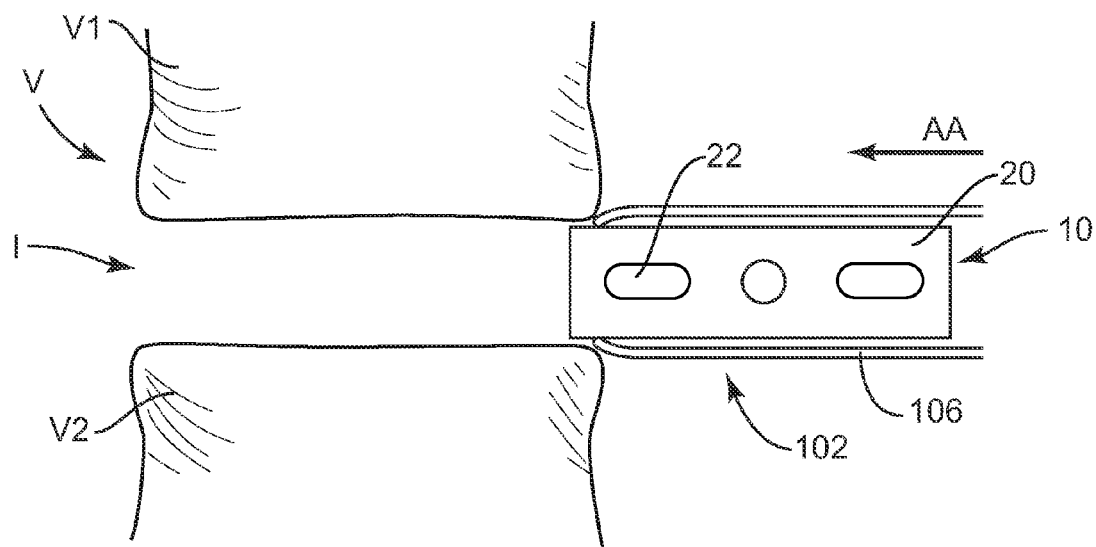
FIG. 15 is a side view of the vertebrae and components of the system shown in FIG. 13 including an implant in accordance with the principles of the present disclosure.
Figure 16:
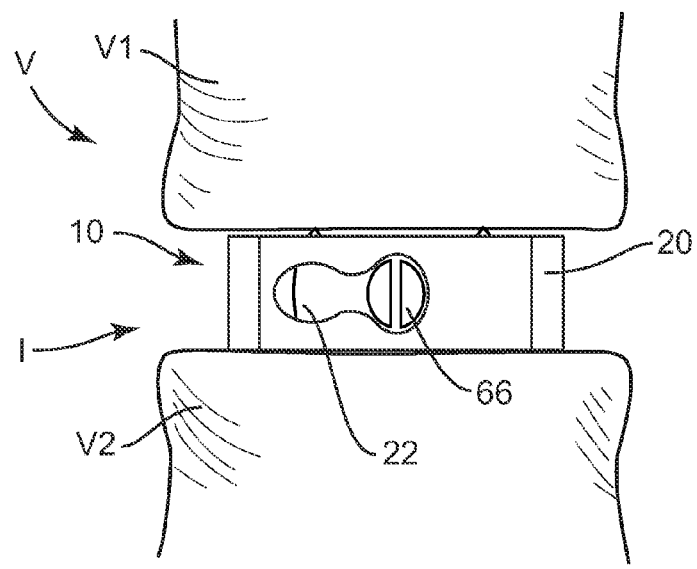
FIG. 16 is a side view of the vertebrae and the implant shown in FIG. 15.

Spinal implant 10, in the first, collapsed configuration, is delivered through surgical pathway 102, as shown in FIG. 15, into intervertebral disc space I with a delivery instrument (not shown) via sleeve 106, as manipulated in the direction of arrow AA. The driver delivers spinal implant 10 into the prepared intervertebral disc space I, between vertebrae V1 and vertebrae V2, according to the requirements of a particular surgical application. Spinal implant 10 is manipulated such that key 64 and/or key 66 are accessible, and that surfaces 26, 28 of frame 20 are oriented to face opposing vertebrae V1, V2, as shown in FIG. 16.

Figure 17:
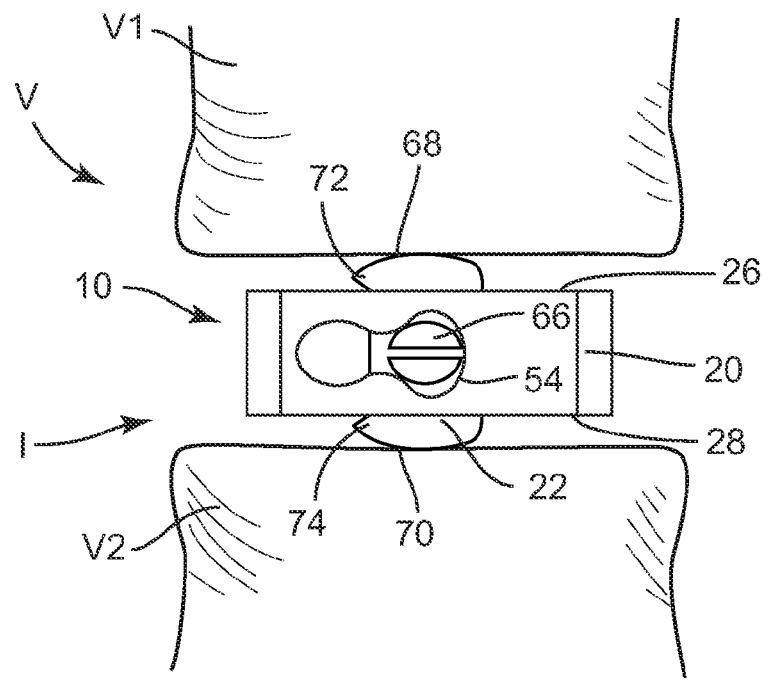
FIG. 17 is a side view of the vertebrae and the implant shown in FIG. 16.
Figure 18:
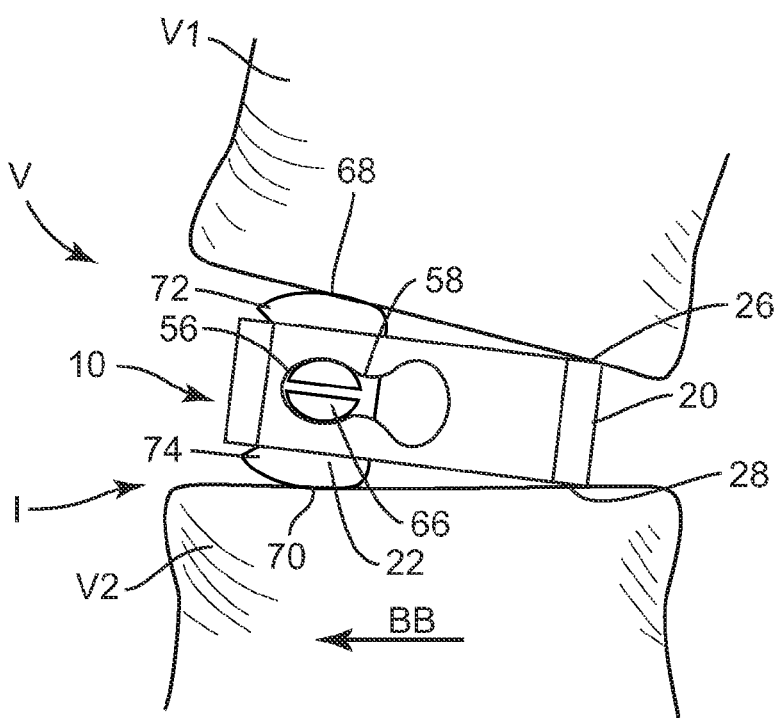
FIG. 18 is a side view of the vertebrae and the implant shown in FIG. 16.

Cam driver 100 (FIG. 20) is delivered to the surgical site through surgical pathway 102 and head 110 is mated with key 64 or key 66. Head 110 fits with the channel of key 64 or key 66 to rotate cam body 22 in a counterclockwise direction, as discussed above, about the center of rotation of spinal implant 10 and axis a. Cam body 22 rotates about axis a such that keys 64, 66 rotate relative to keyways 46, 54 within slots 44, 52, and flanges 72, 74 extend over and engage surfaces 26, 28 respectively, to retain frame 20 in a second configuration, such as, for example, an expanded configuration with cam body 22, as shown in FIG. 17. Vertebra engaging surfaces 68, 70 rotate about axis b of cam body 22 and simultaneously pass through openings 30, 32 to provide an expanded height of spinal implant 10.

In the expanded configuration, head 110 drives cam body 22 in translation relative to frame 20 in a first axial direction, as discussed above. Keys 64, 66 linearly translate in the direction of arrows BB shown in FIG. 18 through slots 44, 52 to distract and/or snap through gates 50, 58 for disposal in keyways 48, 56. Axis b of cam body 22 is spaced apart a distance d (FIG. 2) from axis a of frame 20 in the expanded configuration. The transverse oval configuration of keyways 48, 56, and gates 50, 58 capture keys 64, 66 and prevent rotation and escape of keys 64, 66 from keyways 48, 56. Ranges 72, 74 and gates 50, 58 fixate and lock spinal implant 10 in the expanded configuration. Spinal implant 10 distracts vertebrae V1 and vertebrae V2 to restore height and decompress vertebrae V, restore lordosis, and resist subsidence of surfaces 70, 72 into vertebral endplates and migration of spinal implant 10 within disc space I.

Spinal implant 10 remains in place within disc space I and in engagement with vertebrae V1, V2 to stabilize the area of vertebrae V in accordance with the surgical procedure. The components of implant 10 secure and stabilize vertebrae V in connection with the surgical procedure while preventing undesired migration of spinal implant 10. Spinal implant 10 can be made of radiolucent materials such as polymers. Radiomarkers may be included for identification under x-ray, fluoroscopy, CT or other imaging techniques.

In one embodiment, the interbody implant system includes at least one agent, which may be disposed, packed or layered within, on or about the components and/or surfaces thereof. For example, the at least one agent is configured for disposal within apertures 59, 76. The at least one agent can include bone growth promoting material, such as, for example, bone graft. The bone graft can be a particulate material, which may include an osteoconductive material such as hydroxyapatite and/or an osteoinductive agent such as a bone morphogenic protein (BMP) to enhance bony fixation of spinal implant 10 with the adjacent vertebrae V.

It is contemplated that the bone graft may include therapeutic polynucleotides or polypeptides. It is further contemplated that the bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines.

It is envisioned that the agent may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (bredinin™), brequinar, deoxyspergualin, and azaspirane (SKF 105685), Orthoclone OKT™ (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

Figure 19:
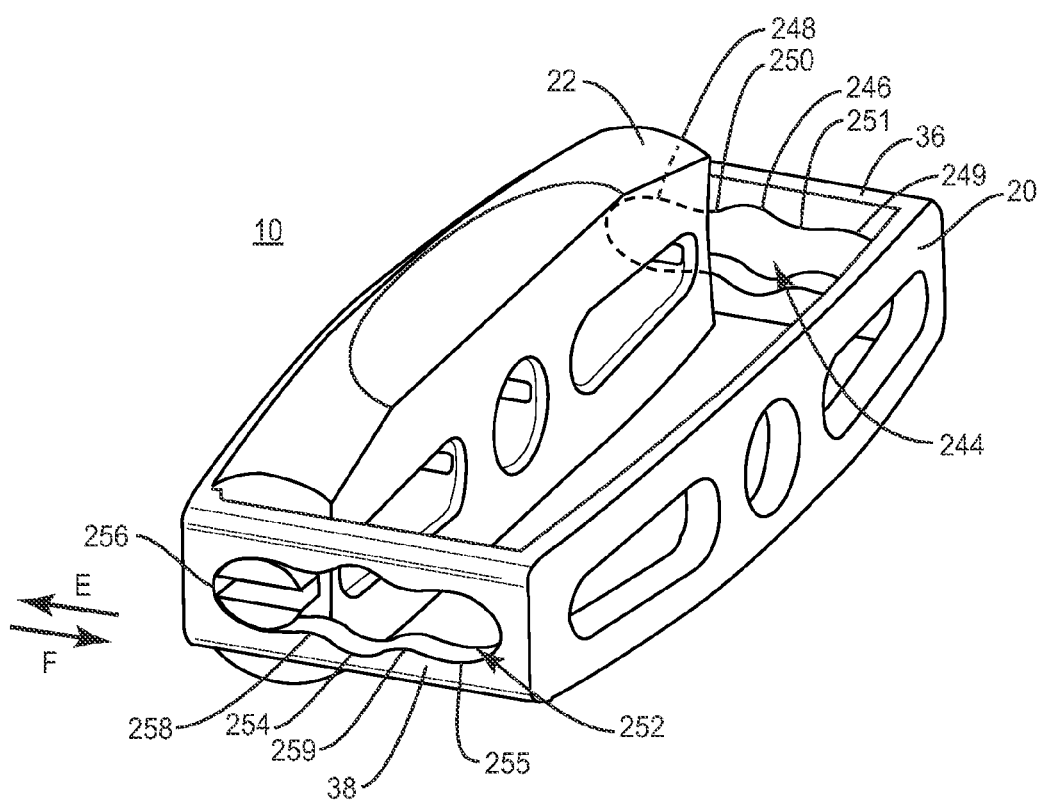
FIG. 19 is a perspective view of one embodiment of a spinal implant in accordance with the principles of the present disclosure.
Figure 20:
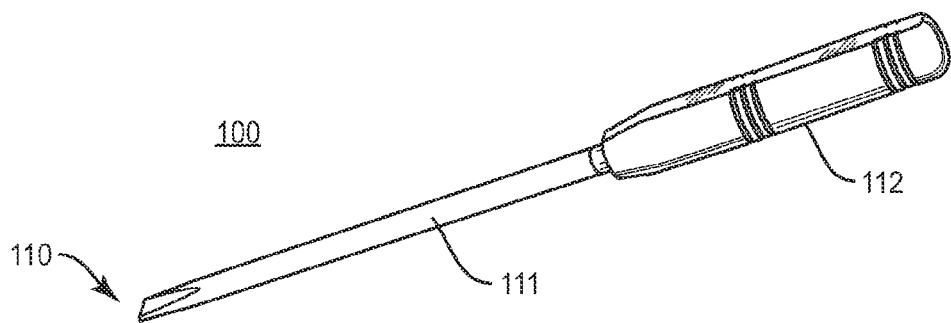
FIG. 20 is a perspective view of an instrument of the system in accordance with the principles of the present disclosure.

In one embodiment, as shown in FIG. 19, spinal implant 10, similar to that described with regard to FIGS. 1-18, is configured for bi-directional translation in a first axial direction shown by arrow E and a second, opposite axial direction shown by arrow F. End wall 36, described above, defines an elongated slot 244 configured to support cam body 22. Slot 244 defines a first keyway 246 having a substantially oval configuration and a second keyway 248 having a substantially oval configuration disposed in transverse orientation relative to keyway 246. Keyway 246 is connected to keyway 248 by a locking element portion of slot 244, such as, for example, gates 250 that provide a reduced dimension of slot 244 to fix cam body 22 in a position and prevent movement of cam body 22 from keyway 248. Slot 244 defines a third keyway 249 having a substantially oval configuration disposed in transverse orientation relative to keyway 246. Keyway 246 is connected to keyway 249 by a locking element portion of slot 244, such as, for example, gates 251 that provide a reduced dimension of slot 244 to fix cam body 22 in a position and prevent movement of cam body 22 from keyway 249.

End wall 38, described above, defines an elongated slot 252 configured to support cam body 22. Slot 252 defines a first keyway 254 having a substantially oval configuration and a second keyway 256 having a substantially oval configuration disposed in transverse orientation relative to keyway 254. Keyway 254 is connected to keyway 256 by a locking element portion of slot 252, such as, for example, gates 258 that provide a reduced dimension of slot 252 to fix cam body 22 in a position and prevent movement of cam body 22 from keyway 256. Slot 252 defines a third keyway 255 disposed in transverse orientation relative to keyway 254. Keyway 254 is connected to keyway 255 by a locking element portion of slot 252, such as, for example, gates 259 that provide a reduced dimension of slot 252 to fix cam body 22 in a position and prevent movement of cam body 22 from keyway 255.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
a first component including a wall that defines a first surface and a second surface, the first surface defining a first opening and the second surface defining a second opening, the second opening being spaced apart from the first opening to define a cavity therebetween;
a second component having a fixed length between opposite first and second ends of the second component, the second component being supported by the first component and configured for movement relative thereto, the second component being movable between a first configuration such that the second component is disposed between the first opening and the second opening within the cavity and a second, expanded configuration such that the second component simultaneously passes through the first and second openings to extend from the cavity,
the wall includes a first end wall having a slot that supports the first end of the second component and a second end wall having a slot that supports the second end of the second component, and
each slot defines a first keyway and a second keyway such that the first and second ends are disposed in a respective first keyway in the first configuration and the second component is moved to the second configuration such that the first and second ends are disposed in a respective second keyway.

2. The spinal implant of claim 1, wherein the second component includes a first wall surface and an opposing second wall surface, which extend along a longitudinal axis defined by the second component such that in the second configuration the first wall surface and the second wall surface simultaneously pass through the first and second openings to extend from the cavity.

3. The spinal implant of claim 2, wherein in the second configuration, the first wall surface is configured for engaging a first vertebral surface and the second wall surface is configured for engaging a second vertebral surface.

4. The spinal implant of claim 1, wherein movement of the second component to the second configuration includes rotation of the second component about a longitudinal axis thereof.

5. The spinal implant of claim 1, wherein movement of the second component to the second configuration includes rotation of the second component about a longitudinal axis thereof and linear translation of the second component relative to the first component.

6. The spinal implant of claim 1, wherein the second component includes at least one fixation element configured to engage at least one of the first surface and the second surface of the first component to fix the first and second components in the second configuration.

7. The spinal implant of claim 6, wherein the at least one fixation element includes a flange configured to engage the first surface of the first component and a flange configured to engage the second surface of the first component.

8. The spinal implant of claim 1, wherein the first and second ends each include a key configured to receive an instrument, the instrument being configured to rotate the second component about a longitudinal axis thereof to the second configuration.

9. The spinal implant of claim 1, wherein each slot is elongated such that the first and second ends of the second component are rotatable and linearly translatable therein.

10. The spinal implant of claim 1, wherein each slot further includes a locking element configured to retain the first and second ends in the second keyway.

11. The spinal implant of claim 1, wherein the first keyway has an oval configuration and the second keyway has an oval configuration disposed in a transverse orientation relative to the first keyway.

12. The spinal implant of claim 1, wherein the first component includes at least one opening configured for disposal of at least one agent.

13. The spinal implant of claim 12, wherein the second component includes at least one opening configured for disposal of at least one agent.

14. An interbody implant system comprising:
a support including a first end wall, a second end wall and at least one side wall extending therebetween, the walls defining a first surface that defines a first opening that is substantially disposed in a first plane and a second surface that defines a second opening that is substantially disposed in a second plane, the second plane being spaced apart from the first plane to define a cavity therebetween, the first end wall and the second end wall each including an elongated slot;
a body defining a longitudinal axis and having a fixed length extending between a first end and a second end, the first end being supported with the slot of the first end wall and the second end being supported with the slot of the second end wall, the body including a first vertebral engaging surface and a second, opposing vertebral engaging surface disposed along the longitudinal axis, the body being disposable between a collapsed configuration such that the first and second vertebral engaging surfaces are disposed in the cavity and an expanded configuration such that the body is rotated about the longitudinal axis such that the first and second vertebral engaging surfaces pass through the first and second openings of the support and the body linearly translates relative to the support;
an instrument including an engagement member configured to engage at least one of the first end and the second end of the body and rotate the body about the longitudinal axis; and at least one agent configured for disposal with at least one aperture of the support and the body, and
each slot defines a first keyway and a second keyway such that the first and second ends of the body are disposed in a respective first keyway in the first configuration and the first and second ends of the body are disposed in a respective second keyway in the second configuration.

15. The interbody implant system of claim 14, wherein each slot further includes a locking element configured to retain the first and second ends of the body in the second keyway.

16. An interbody implant system comprising:
a support frame defining a central longitudinal axis and including a first end wall and a second end wall disposed in substantially parallel relation, the first and second end walls being connected by spaced apart side walls, the walls of the support frame defining an upper surface and a lower surface, the upper surface defining an upper opening and the lower surface defining a lower opening, the upper opening being spaced apart from the lower opening to define a cavity therebetween, the first end wall and the second end wall each defining a slot, each slot defining a first keyway, a second keyway and a locking element;
a cam body defining a longitudinal axis and extending between a first end supported in the slot of the first end wall and a second end supported in the slot of the second end wall, the cam body including a first surface configured to engage a first vertebral surface and a second surface configured to engage a second vertebral surface, the cam body further including a first flange configured to engage the upper surface of the support frame and a second flange configured to engage the lower surface, the cam body being disposable between a collapsed configuration such that the first and second vertebral surfaces are substantially disposed in the cavity and the longitudinal axis of the cam body is disposed in a coaxial orientation with the central longitudinal axis of the support frame, and movable to an expanded configuration such that the first and second ends of the cam body are rotatable in the first keyways such that the body is rotated about the longitudinal axis such that the first and second vertebral engaging surfaces pass through the first and second openings of the support frame and the first and second ends are linearly translatable to the second keyways and retained therein by the locking elements and the flanges engage the upper and lower surfaces respectively to fix the support frame and the cam body in the expanded configuration;
a cam driver engagable with at least one of the first end and the second end of the cam body to rotate the cam body; and
at least one agent configured for disposal with at least one aperture of the support frame and at least one aperture of the cam body.

* * * * *